United States Patent
Seay et al.

[11] Patent Number: 5,651,671
[45] Date of Patent: Jul. 29, 1997

[54] ORTHODONTIA ANALYTICAL SYSTEM

[76] Inventors: William J. Seay, 6325 Barberry Hill Dr., Gainesville, Ga. 30506; Alex Jacobsen, 3605 Dover Ct., Birmingham, Ala. 35223

[21] Appl. No.: 439,868
[22] Filed: May 12, 1995
[51] Int. Cl.$^6$ ............................................. A61C 7/06
[52] U.S. Cl. ............................................. 433/5
[58] Field of Search ............................... 433/5, 6

[56] References Cited

U.S. PATENT DOCUMENTS

| | | | |
|---|---|---|---|
| 3,533,163 | 10/1970 | Kirschenbaum | 433/5 |
| 3,648,372 | 3/1972 | Kirschenbaum | 433/5 |
| 3,885,310 | 5/1975 | Northcutt | 433/5 |
| 4,238,188 | 12/1980 | Armstrong | 433/5 |
| 4,255,138 | 3/1981 | Frohn | 433/6 |
| 4,629,424 | 12/1986 | Lauks et al. | 433/6 |
| 4,707,086 | 11/1987 | Armstrong et al. | 433/5 |
| 5,245,592 | 9/1993 | Kuemmel et al. | 433/6 |

*Primary Examiner*—Edgar S. Burr
*Assistant Examiner*—Daniel J. Colilla
*Attorney, Agent, or Firm*—Harry I. Leon

[57] ABSTRACT

A device for applying a force to an orthodontic apparatus in such a manner as to allow a patient or his orthodontist to adjust the force and for recording the force as a function of the time the apparatus is actually worn. In the device, two similar compression springs are arrayed in parallel with one end of each spring pushing against a movable saddle disposed distal from the patient's jaw. The opposite end of each spring abuts a stop which together with the springs and saddle is housed within a case. Belts which extend around the user's head and/or neck hold the case as well as the stop housed therein in fixed position during use. After the device is placed on the patient, the extension of each spring can be adjusted by repositioning the stop. The movable saddle, on the other hand, is fastened to one end of a strap connected to the orthodontic apparatus. Pulling the strap further compresses the two springs between the saddle and the stop. The force exerted by the springs on the strap is measured by tracking the movement of the saddle. When a force above a predetermined setpoint is applied, a solid state timing unit is activated. The device also contains a solid state memory for storing the patient's force/time history between office visits. Accessible through an IR window formed in the case, data stored in the memory can be retrieved for immediate review by a portable memory readout unit.

4 Claims, 22 Drawing Sheets

Patient Listing:

ADDISON
AIKINS
BASSINGER
BENNET
BJORNSON
BLESER
BOLAN
BUNNY
BURNS
BYERS
CANADY
CARLSON
CASTEEL
COYOTE
DENNISSON

Current Patient: CARLSON

☐ Add a visit
☐ Show info textually
☐ Show info graphically
☐ Add a new patient

Ok     Quit

*Fig. 12.*

Doctor: Ortho Dontist          Date: 02/07/95
Patient Name: CARLSON, MIKE
Patient #: 1

| Exam Date | Time Worn | Exam Interval | Force (Oz.) |
|---|---|---|---|
| 10/09/95 | 108h 20m | 15 | 7 |
| 09/25/95 | 135h 00m | 18 | 7 |
| 09/07/95 | 098h 20m | 16 | 7 |
| 08/22/95 | 098h 20m | 14 | 7 |
| 08/08/95 | 098h 20m | 14 | 7 |
| 07/25/95 | 097h 30m | 15 | 7 |
| 07/10/95 | 097h 30m | 14 | 7 |
| 06/27/95 | 096h 40m | 14 | 7 |
| 06/13/95 | 096h 40m | 14 | 7 |
| 05/30/95 | 096h 40m | 14 | 7 |
| 05/16/95 | 097h 30m | 14 | 7 |
| 05/02/95 | 096h 40m | 15 | 7 |
| 04/18/95 | 097h 30m | 14 | 7 |
| 04/04/95 | 105h 50m | 18 | 5 |
| 03/17/95 | 113h 20m | 18 | 5 |
| 02/30/95 | 088h 20m | 12 | 5 |
| 02/18/95 | 085h 00m | 11 | 5 |
| 02/07/95 | 000h 00m | 0 | 5 |
| TOTALS: | 1707h 30m | 256 | |

Fig. 13.

Print   Ok

ORTHODONTIA ANALYTICAL SYSTEM

BACKGROUND OF THE INVENTION

In orthodontic care, a small amount of directed force is applied to malaligned teeth over a period of time, slowly moving the teeth into proper alignment. This force can be supplied by springs external to the mouth, that is, extraorally.

In U.S. Pat. No. 4,416,625, which issued Nov. 22, 1983, Armstrong utilizes an extension spring to supply extraoral force. Armstrong provides multiple spring end supports which can be used to stretch the spring to varying degrees, depending upon the amount of extraoral force needed.

In a subsequent patent, U.S. Pat. No. 4,553,934, which issued Nov. 19, 1985, Armstrong and Houser disclose means utilizing a compression spring to supply the extraoral force. A strap, which, when worn, ultimately applies force to a user's teeth, is attached to a rod passing through this spring. Distal ends thereof are attached to the rod and abut a sleeve, respectively; the position of the sleeve, which is adjustably mounted, determines the degree of compression applied to the spring, varying the extraoral force. The compression load on the spring can also be changed by adjusting the strap.

To be effective, an orthodontic device must be worn over an extended period of time each day. Further, orthodontists, in many cases, guarantee that they will be able to align a patient's teeth. For both purposes, it is desirable to record how long a patient actually wears an orthodontic device and the extraoral force exerted. Unfortunately, an orthodontic device that has means for measuring the force applied as a function of time is not available in the prior art.

SUMMARY OF THE INVENTION

The principal object of the present invention is to provide an orthodontic care device capable of applying an extraoral force to a patient's jaw/teeth and of recording the force applied thereto as a function of the time the device is actually worn.

A further object of this invention is to provide a memory readout unit capable of reading the force/time history recorded by said orthodontic care device and storing this history, possibly with other previously stored force/time histories, for future retrieval.

A still further object is to provide means, such as a serial or parallel port, for downloading information stored in the memory readout unit into a computer so that the information can be analyzed, utilizing a suitable computer program, and printed out in a convenient format for review by an orthodontist and his patients.

In accordance with the present invention, there is provided an orthodontia system comprising an orthodontic care device and a memory readout unit. The device includes a case in which is housed at least one spring biased in compression, a movable saddle and an adjustable stop, with opposite ends of the spring abutting the saddle and stop, respectively. Orthodontic headgear, such as a headcap or neckband which extend around a patient's head or neck, respectively, hold the case as well as the stop in place during use. When the device is being worn, the end of the spring which pushes against the movable saddle is disposed distal from the patient's jaw. A strap attached to the movable saddle connects the device to the outer bow of an orthodontic apparatus, secured, in the conventional manner, by an inner bow to the patient's teeth/jaw. Pulling the strap compresses the spring between the saddle and the stop. The case includes structural elements for guiding movements of the spring and strap.

The amount of force which the device applies to the outer bow, and ultimately to a user's teeth/jaw, is, in large part, determined once the outer bow has been properly hooked into any one of several holes formed in the strap. When the device has been strapped on the patient, the extraoral force can be adjusted by repositioning the stop using a screw threadedly engaged with the case. As the screw is tightened, the extension of the spring decreases and the extraoral force increases.

In the preferred embodiment, the force exerted by the spring on the strap is measured indirectly by sensing changes in the magnetic field of a magnet embedded in the strap near the saddle. A solid state Hall effect magnetic flux sensor mounted on an arm rigidly attached to the stop is employed to detect these changes and produce a voltage proportional in magnitude to them. Preferably, the output of the Hall effect sensor is calibrated in ounces of force.

Alternately, the force can be measured using a strain gauge applied to the movable saddle.

Circuits which support the output of the magnetic flux sensor and convert it into a force reading are contained in an electronic circuit board also housed in the case, as is a battery. Additionally, the circuit board contains a solid state timing unit with a real time clock and memory chips for storing a record of the force applied as a function of time. In the preferred embodiment, each such record can be stored for a period that corresponds roughly to the time interval between a patient's visits to his orthodontist, ordinarily about 45 days.

In use, the solid state timing unit is activated when extraoral force in excess of a predetermined setpoint is applied. The real time clock is usually started when the extraoral force exceeds about 4 ounces.

An IR transmitter housed in the case and accessible through an IR window formed therein is provided for transferring the force/time record(s) stored in the memory chips of the orthodontic care device to the memory readout unit. Each such record can be retrieved for immediate review by the memory readout unit and then, if need be, downloaded therefrom into a compatible computer for further processing.

In the preferred embodiment, the memory readout unit comprises means, including an IR window, for communicating with the IR transmitter of the orthodontic care device. Using the memory readout unit, an orthodontist can readily obtain a complete history of his patient's use of the orthodontic care device. Moreover, the force/time records of multiple patients can be read by and stored in the memory readout unit.

To facilitate downloading information from the memory readout unit into most computers, the memory readout unit is preferably equipped with a serial port connection. Once introduced into a computer supported by suitable software, the information can be processed into a convenient format for use by the orthodontist and/or his patients.

BRIEF DESCRIPTION OF THE DRAWINGS

FIGS. 12, 13 and 14 show a typical computer menu for selecting a specific patient's record, his or her record in tabular form, and the record in graphical form, respectively.

DETAILED DESCRIPTION OF THE INVENTION

An orthodontia analytical system comprises a force-transmitting/force history-recording device and a memory readout with computer link which are referred to generally by reference numbers 10 and 40, respectively.

Figure 1:
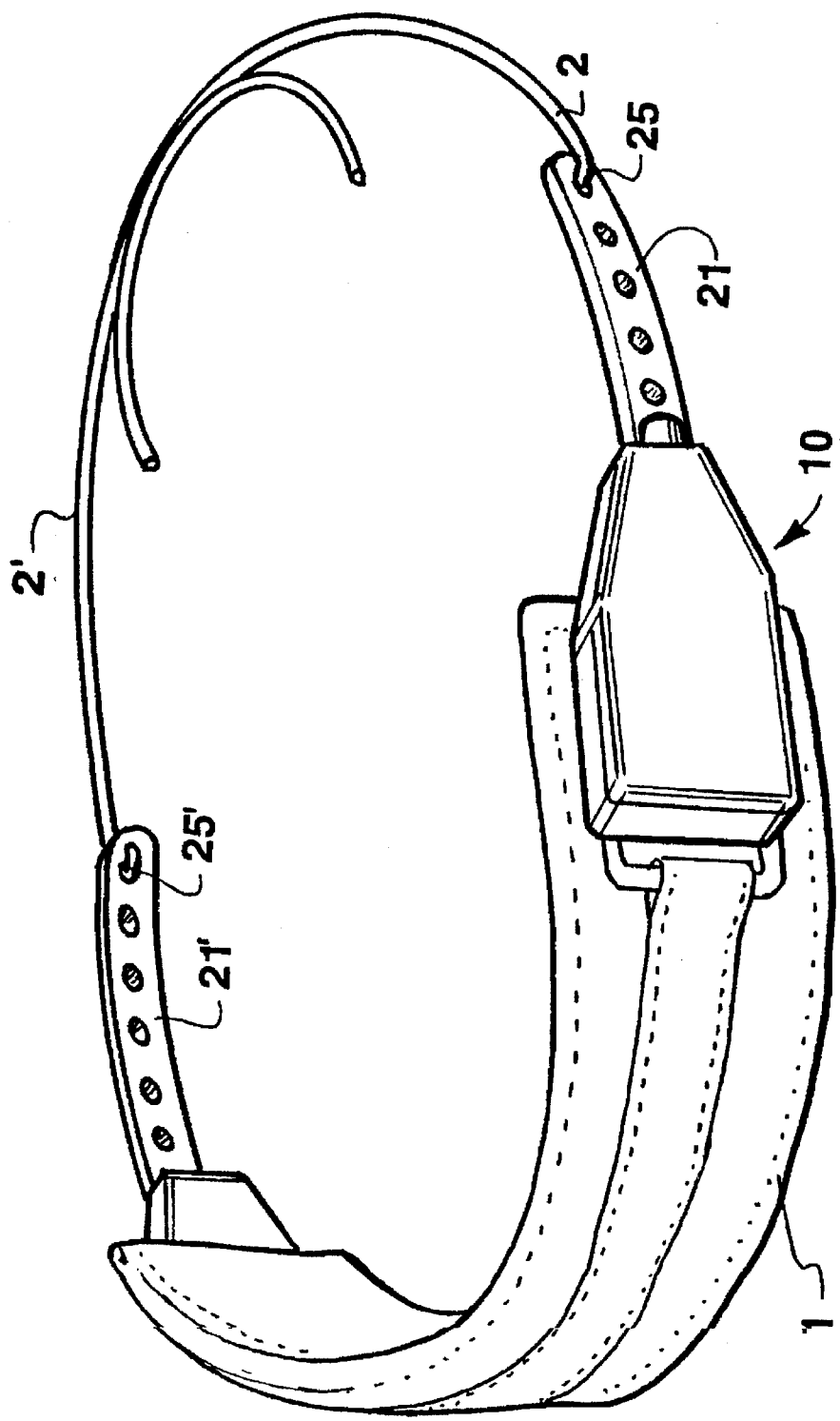
FIG. 1 is a perspective view of the orthodontic care device which is a component of the system according to the present invention, the device being mounted on a neckband or, alternately, on a headband and attached to an orthodontic outer bow.
Figure 2:
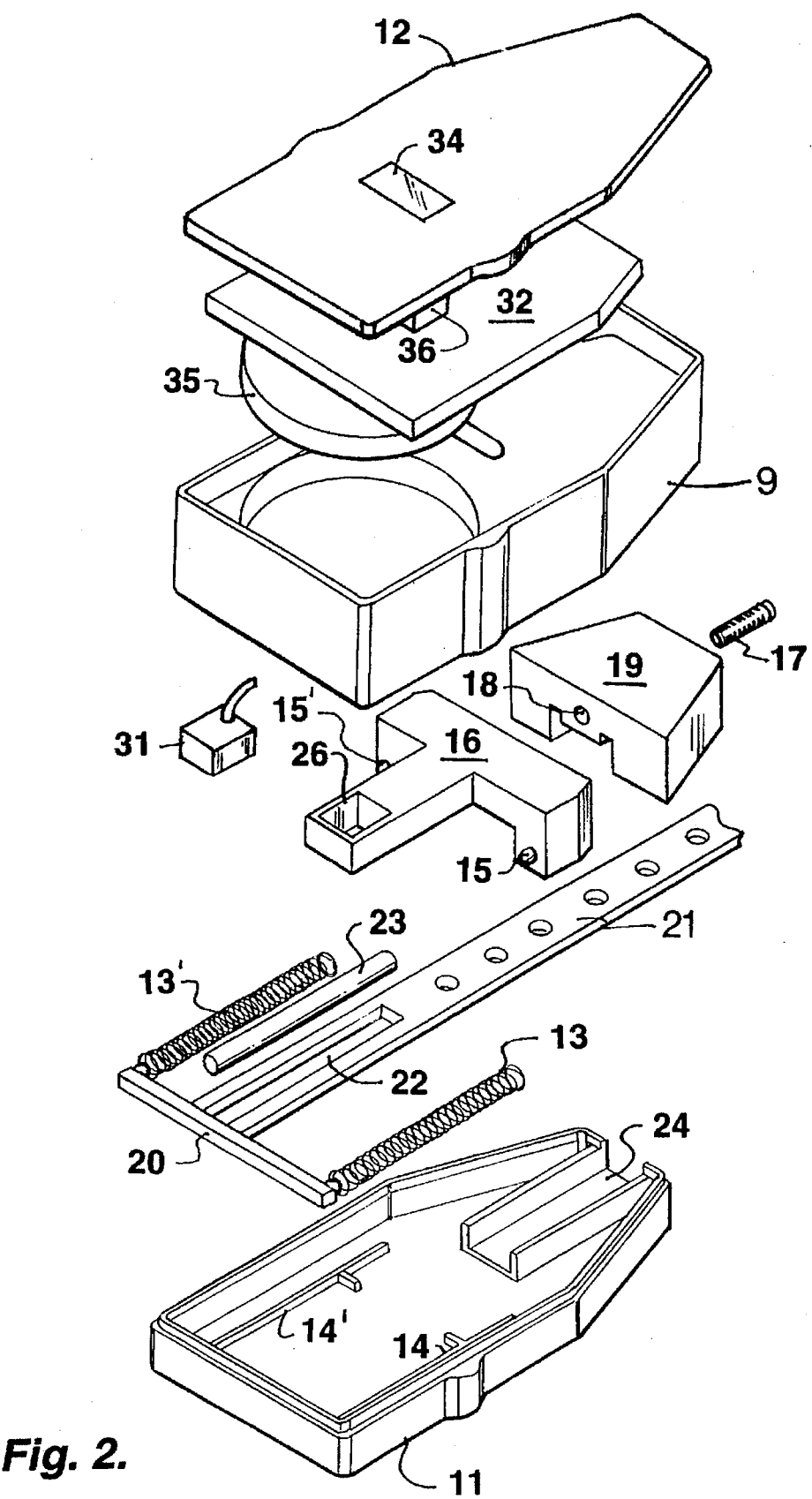
FIG. 2 is an exploded perspective view of the device according to FIG. 1.
Figure 5:
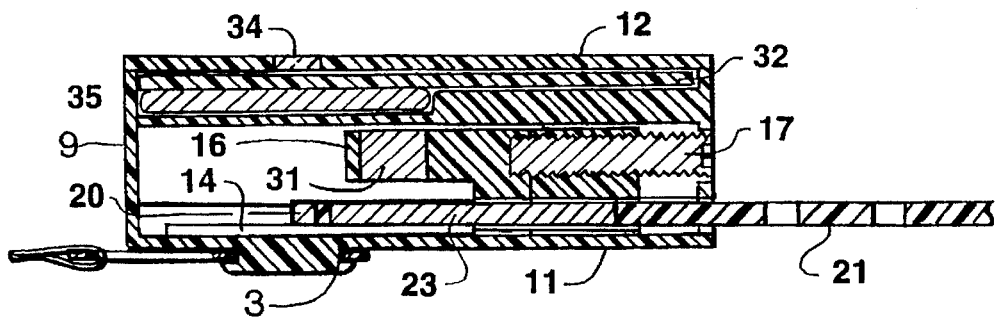
FIG. 5 is a cross-section along line 5—5 of FIG. 3.
Figure 4:
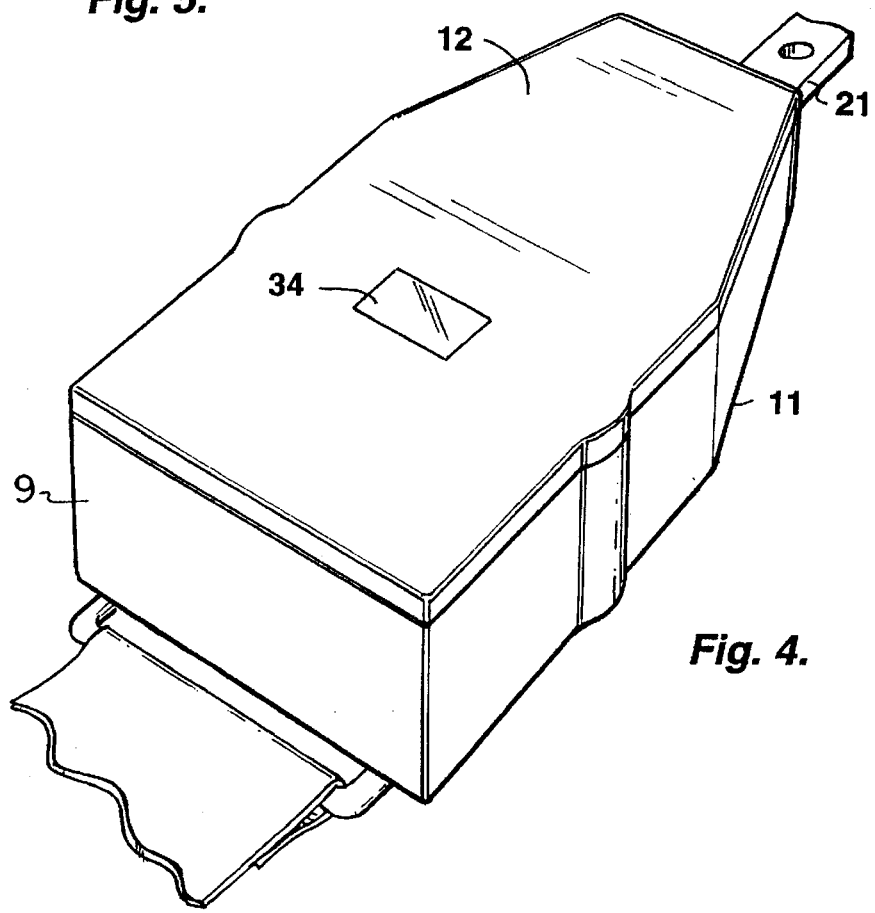
FIG. 4 is a perspective view of the top right side of the device according to FIG. 1.
Figure 3:
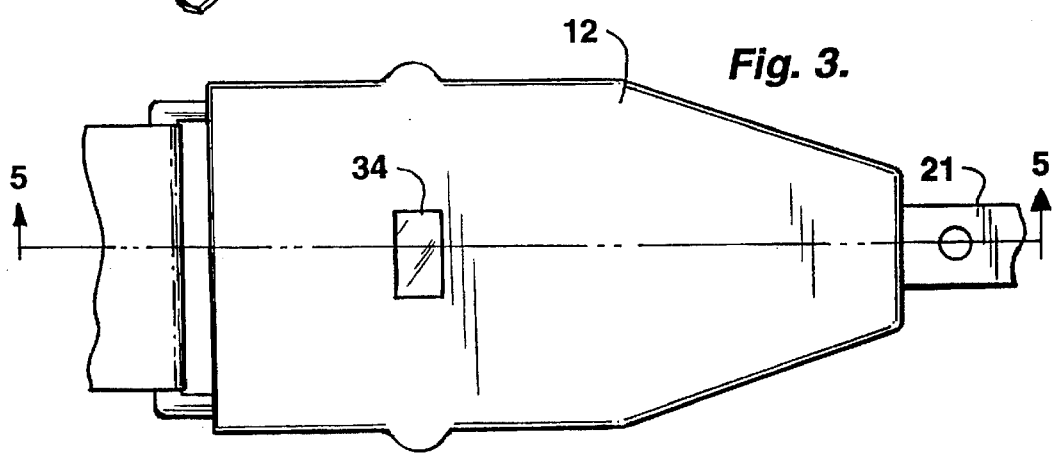
FIG. 3 is a top plan view of the device according to FIG. 1.

A pair of devices 10 are mounted on a neckband 1 or, alternately, on a headband (not shown) and attached to a pair of orthodontic outer bows 2, 2'. The outer bows 2, 2' are themselves fastened to an inner bow (not shown) in contact with a patient's teeth. In the preferred embodiment, each device 10 comprises a case having a top plate 12 and central and lower housing modules 9, 11, which, in assembled relation, are press-fitted together. The module 9 includes means for holding the battery 35. The neckband 1 is attached to the case by a conventional clip breakaway attachment mount 3 secured to the lower housing module 11 (FIG. 5).

Arrayed in parallel within the module 11 are two elongated springs 13, 13' which are biased in compression. Guides 14, 14' formed in the module 11 limit lateral movement of these springs. Both ends of the springs 13, 13' are also constrained, with one end of each spring abutting a face 15, 15' on a stop 16 and the other end pushing against a movable saddle 20.

A screw 17, which threadedly engages a block 19 wedged between the central and lower modules 9, 11, is employed to fix the location of the stop 16. Inserted into an hole 18 formed in the block 19, the screw 17 is advanced therethrough until it pushes against the stop 16 and protrudes from the block. The greater the extent to which the screw 17 protrudes the greater the compression forces on the springs 13, 13'. Preferably, the screw 17 is turned using either an Allen or torx head.

Distal from the stop 16, an end of each spring 13, 13' pushes against a saddle 20 attached by a strap 21, 21' to an outer bow 2, 2' of an orthodontic apparatus. Mounting holes 25, 25' formed in the strap 21 provide means for securing the outer bow 2, 2' to the strap. The strap 21, 21' which moves within a guide channel 24 formed in the module 11, transmits force to the bow 2, 2' from the springs 13, 13' as they are compressed between the stop 16 and the saddle 20 by the strap pulling thereon.

Means for measuring the force applied to the outer bow 2, 2' comprises an elongated magnet 23 and a Hall effect magnetic flux sensor 31. The magnet 23, which is mounted on the strap 21 within an opening 22 formed therein, moves with the strap 21 when load is applied to the outer bow 2, 2'. The sensor 31, mounted on an arm 16 within an aperture 26 formed therein, is disposed proximate with the magnet 23. The sensor 31 detects changes in the magnetic field of the magnet 23 and it moves with the strap 21, 21' these changes can be correlated with the force output of each spring 13, 13', which is a function of its extension and of the longitudinal displacement of the strap.

Figure 6:
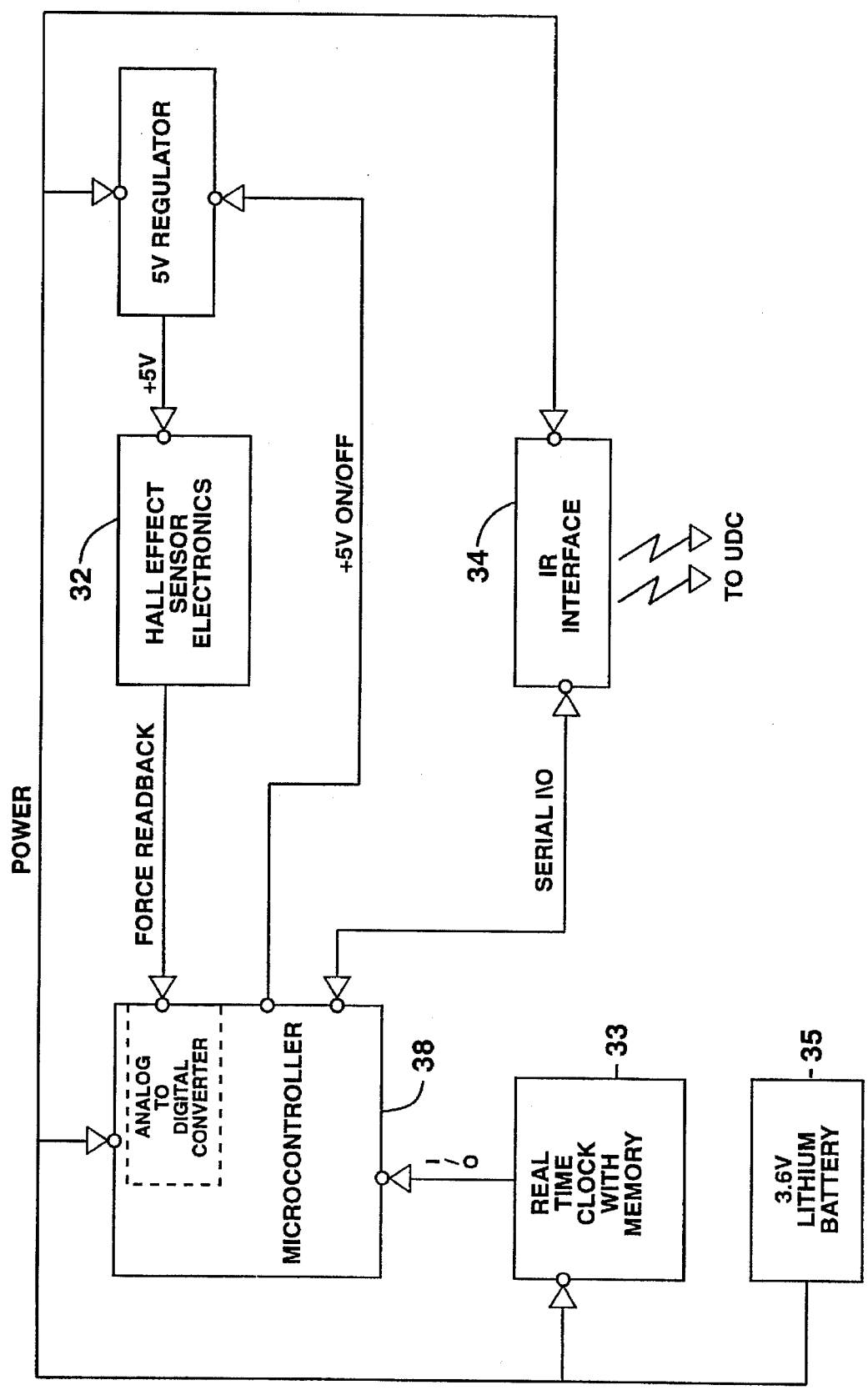
FIG. 6 is a schematic diagram of the circuit in the device according to FIG. 1.

Specifically, a component 32 of a circuit shown schematically in FIG. 6 is employed to relate changes in magnetic flux detected by the sensor 31 to changes in compression forces acting on the springs 13, 13'. The circuit 30 is preferably calibrated so that extraoral force applied to the orthodontic device can be read directly.

In addition, part of the circuit shown in FIG. 6 is a timer/memory circuit 33 which relates real time to a microcontroller 38. The microcontroller 38 pairs force and time data together and stores the result in the memory 33. Moreover, to activate the timer/memory circuit 33, an extraoral force in excess of a predetermined threshold amount must be applied to the strap 21, 21'. Usually, this threshold force is set at about 4 ounces; however, the threshold can be re-set by advancing or retracting the screw 17. The time of wear is considered to be the length of time the extraoral force exceeds the threshold. Preferably, the memory section can store information for at least 45 days.

A wiring diagram for the device 10 is shown schematically in FIG. 6, and the actual wiring is shown in FIG. 10. (FIG. 10 is shown in four parts as FIGS. 10A–10D.)

The memory readout unit 40 is employed to measure, in real time, the extraoral force as it being applied and to read the memory 33 of the device 10. The unit 40 can store in its own memory 54 the force/time histories transferred to it from at least one device 10 and preferably from a multitude of devices 10. With the preferred embodiment, an orthodontist can store all of his patient' records in one memory readout unit 40. The unit 40 has means, including an IR window 44, for communicating with an IR interface 34 in the device 10 through its IR window 36 and for transferring information in the memory 33 to a memory 54 in the unit 40.

Figure 8:
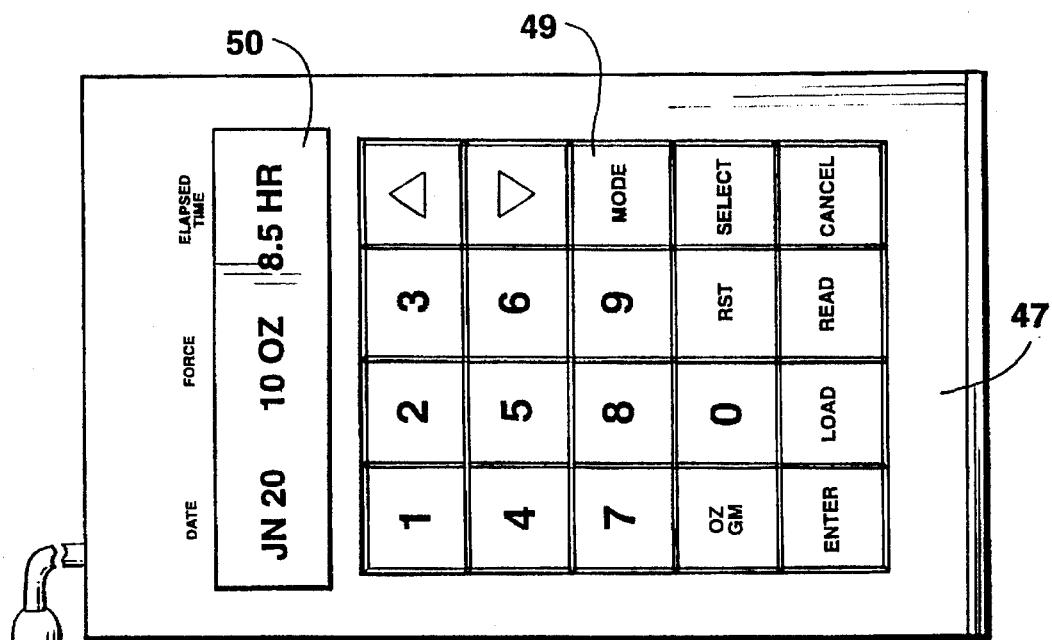
FIG. 8 is a plan view of the memory readout unit according to FIG. 7.
Figure 7:
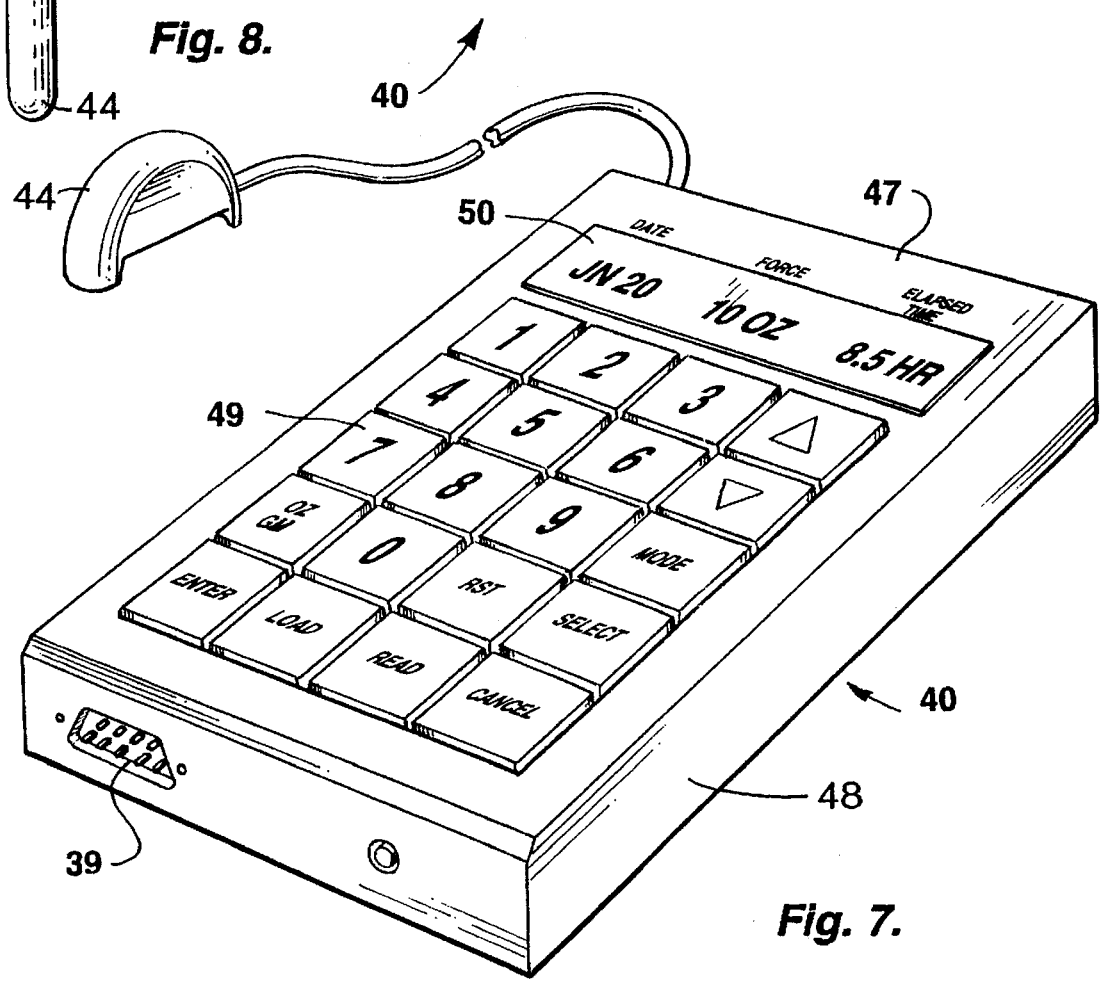
FIG. 7 is a perspective view of the top right side of the memory readout unit which is a component of the system according to the present invention.

The memory readout unit 40 shown in FIGS. 7 and 8 measures, by way of example, approximately six and a half inches in height and four inches in width and has a thickness of about one and a half inches. The unit 40 includes a keyboard 49 mounted on an upper panel 47 of the housing member 48. A display 50, having 16 to 32 characters and visible through an aperture in the upper panel 47, is mounted atop a printed circuit board (not shown). The circuit board, together with other major electrical components mounted thereon, is housed within the member 48.

Figure 14:
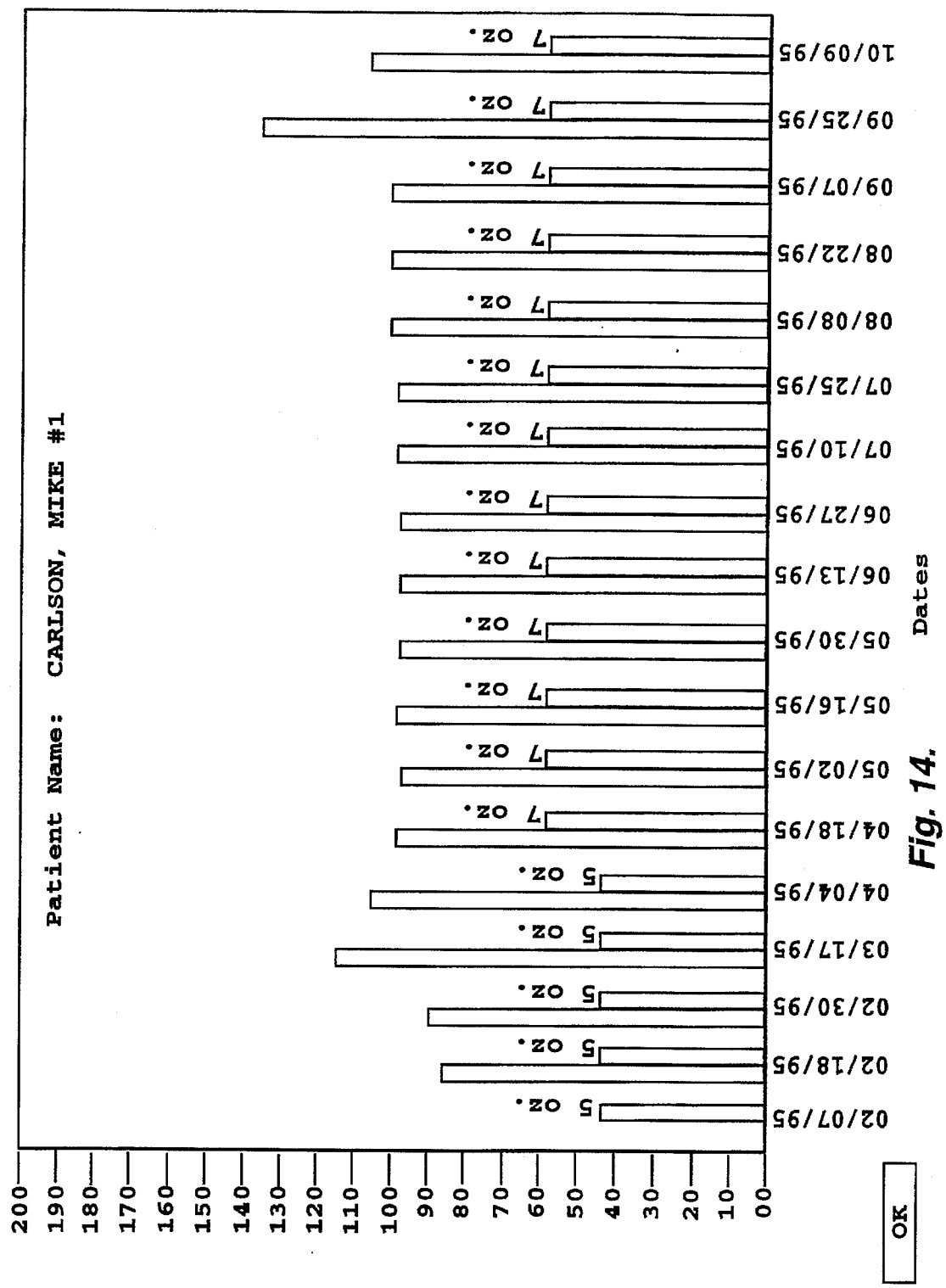

In the preferred embodiment, the memory readout unit 40 is equipped with a standard connector 39, such as a serial port, to facilitate downloading memory from the unit into a compatible computer. To process data after it has been downloaded, the computer is preferably supported by suitable software such as LOTUS 1-2-3® or a similar spread sheet software. A sample of data from the unit 40, as this data undergoes such processing, is shown in FIGS. 12–14. In the menu mode, information is added to a specific patient's record (FIG. 12). A typical readout of his or her record is shown in tabular form in FIG. 13 and in graphical form in FIG. 14.

Figure 9:
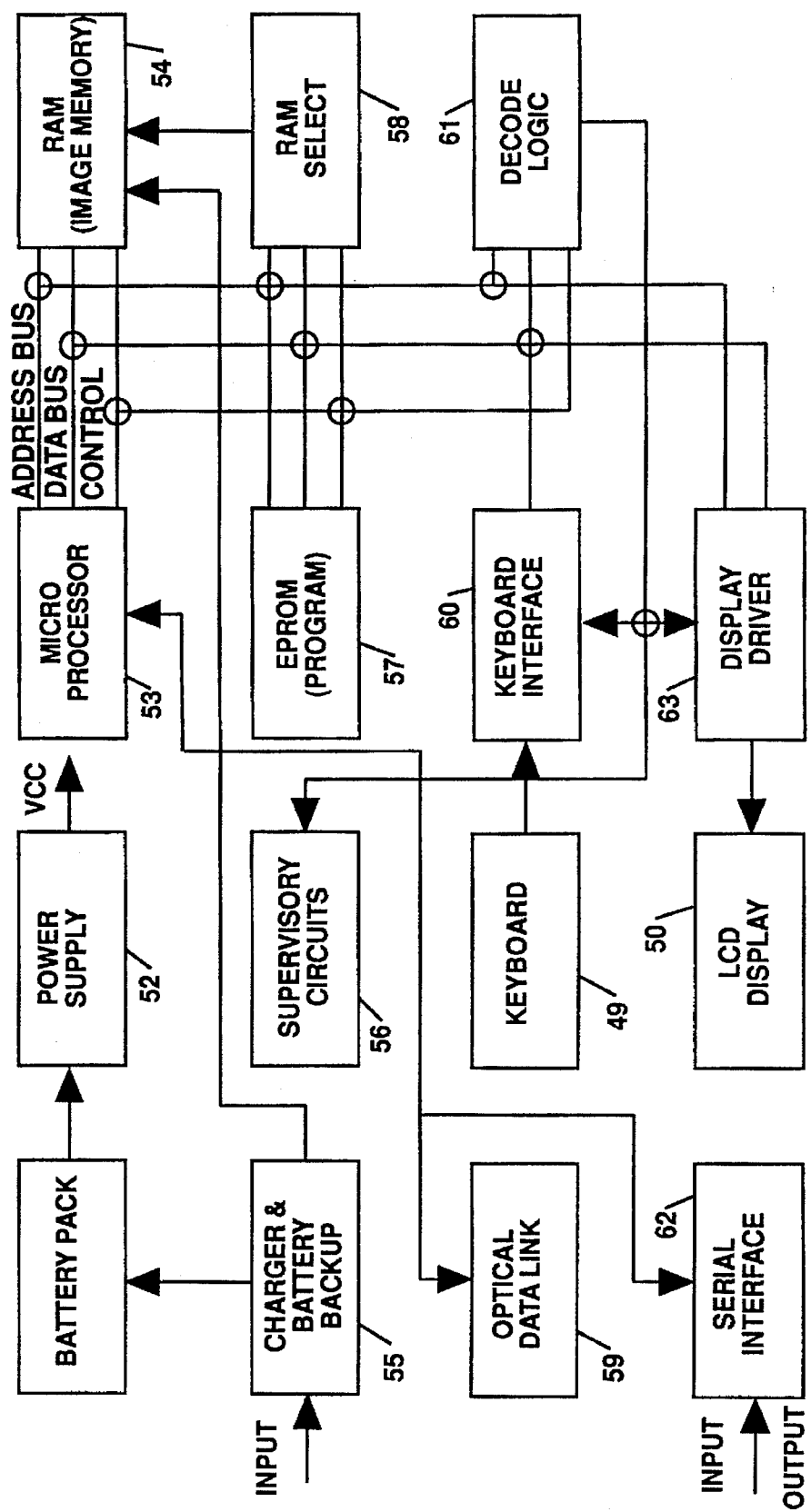
FIG. 9 is a schematic diagram of the circuit for the memory readout unit according to FIG. 7.
Figure 10A:
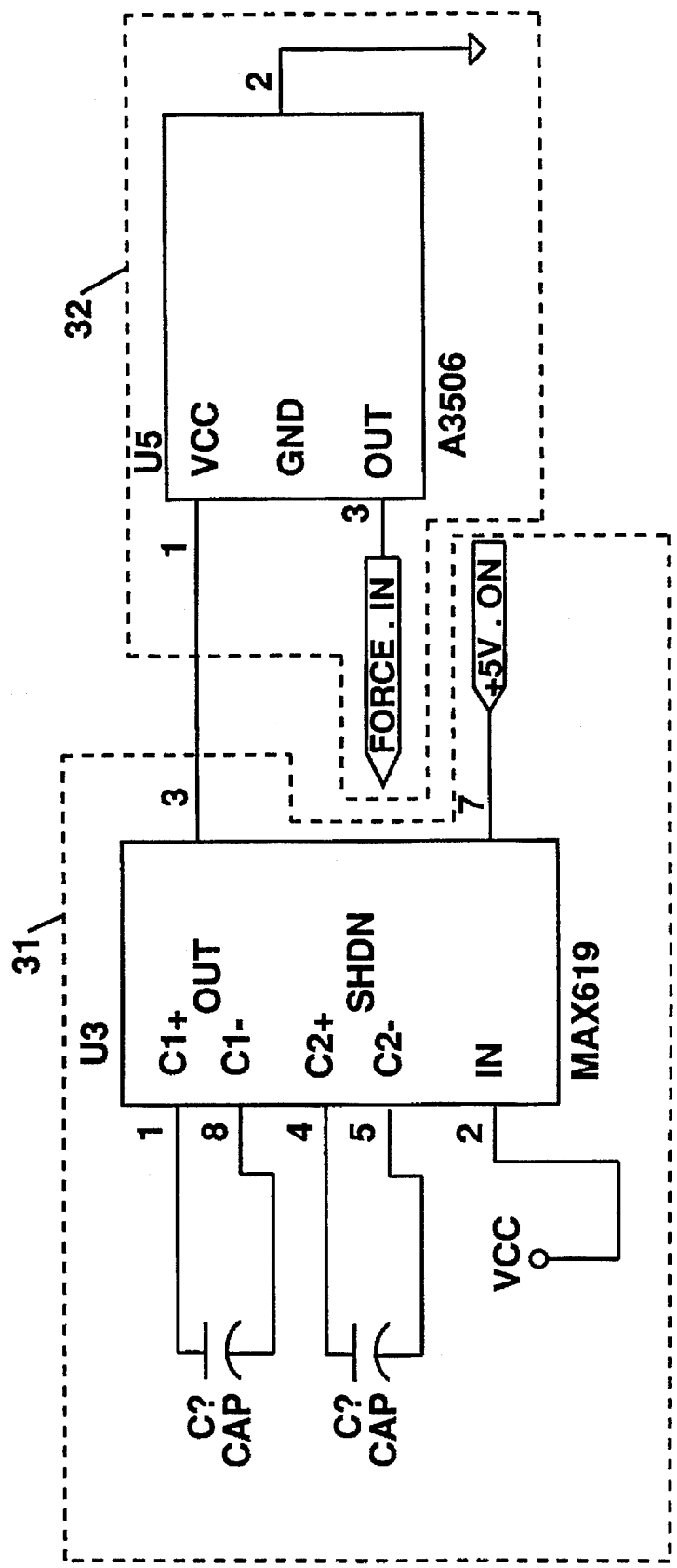
FIGS. 10A–10D, when assembled as one drawing, comprise a wiring diagram of the circuit, shown schematically in FIG. 6, for the orthodontic care device, the numbers within the dashed lines referring to the circuit only and not to other elements of the system according to the present invention.
Figure 10B:
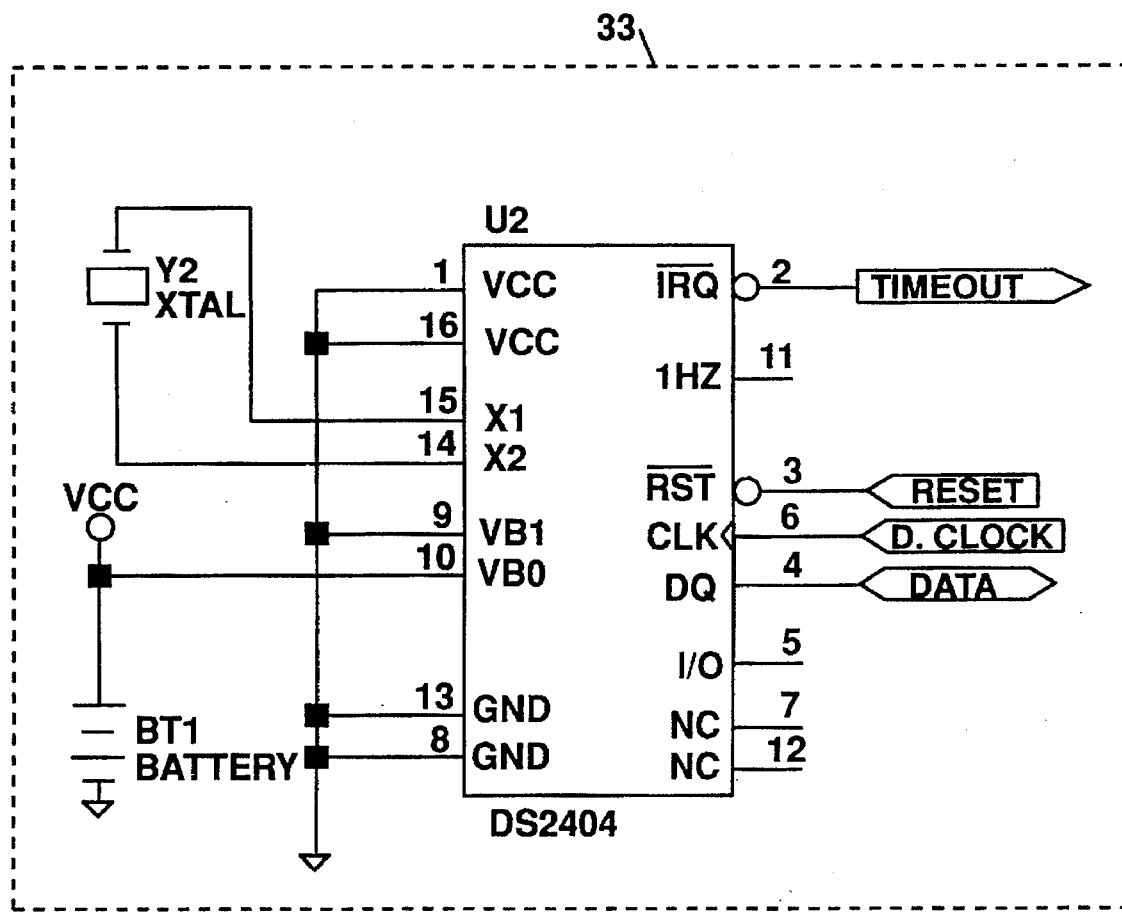
Figure 10C:
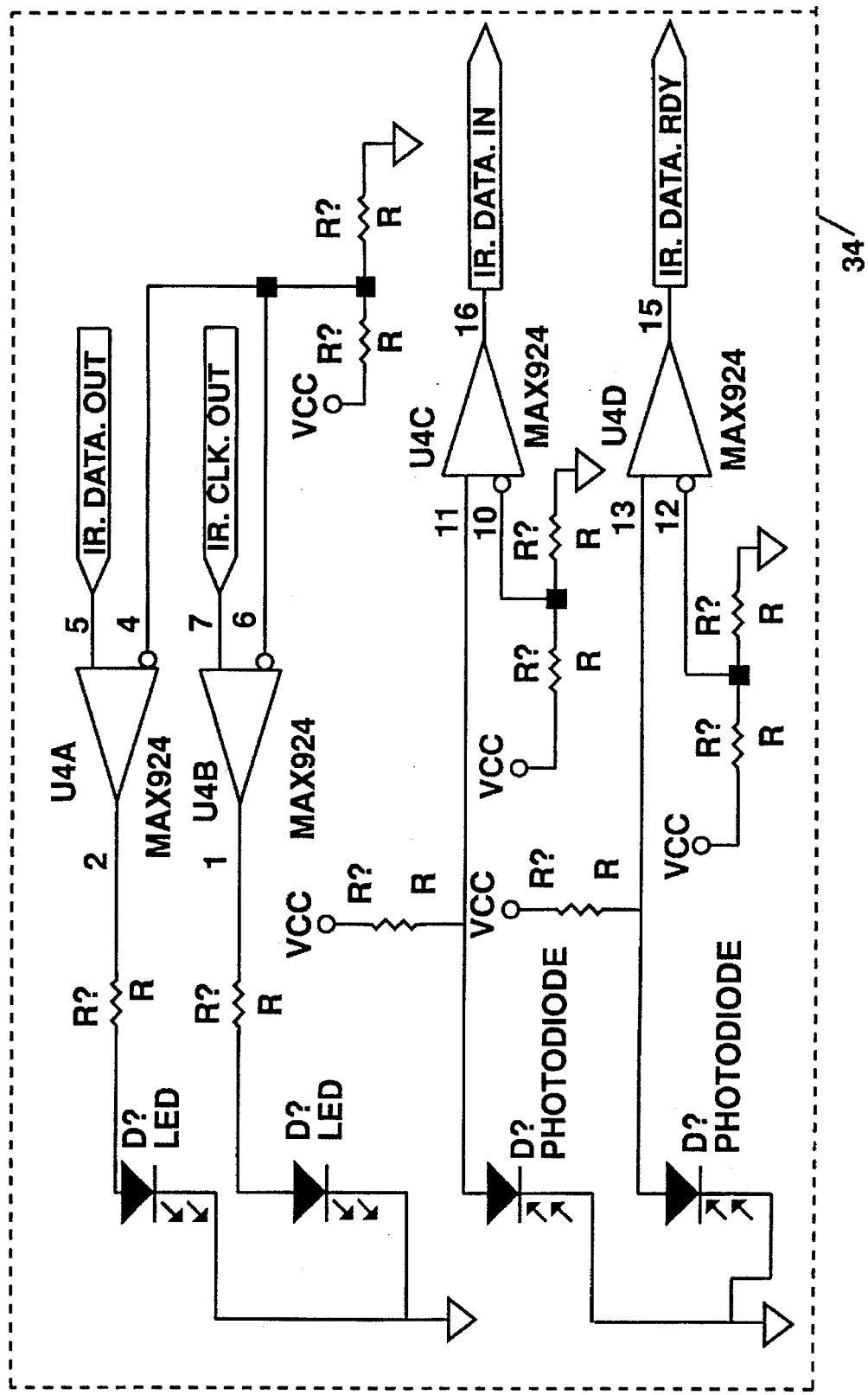
Figure 10D:
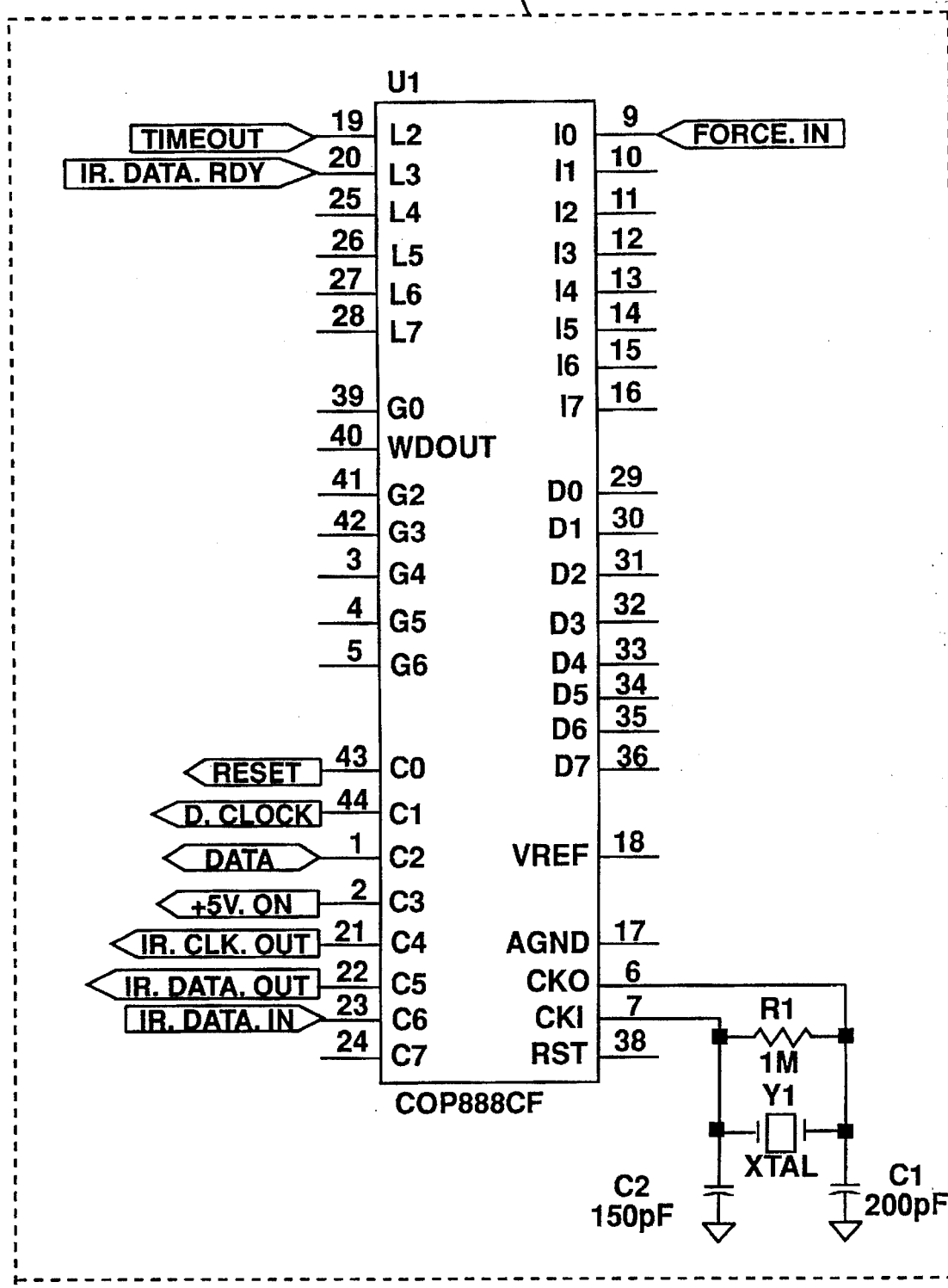
Figure 11A:
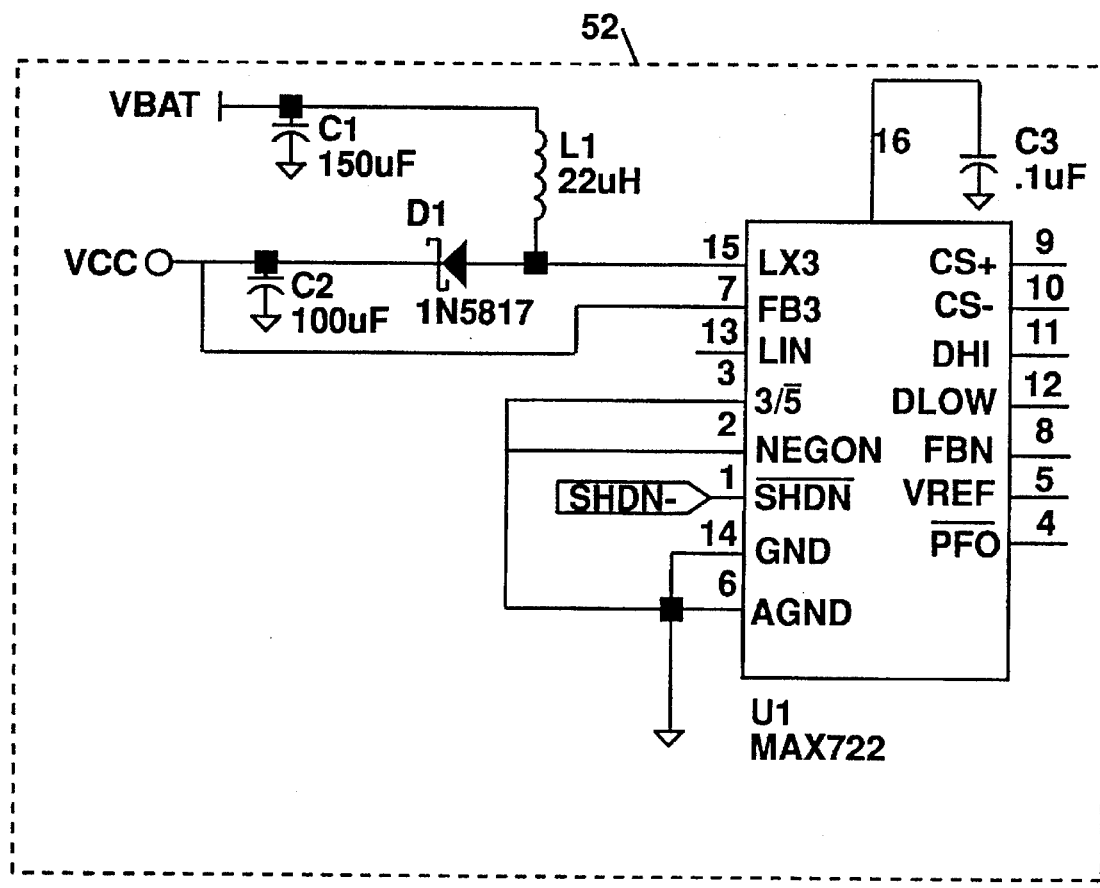
FIGS. 11A–11I, when assembled as one drawing, comprise a wiring diagram of the circuit, shown schematically in FIG. 9, for the memory readout unit, the numbers within the dashed lines referring to the circuit only and not to other elements of the system according to the present invention.
Figure 11B:
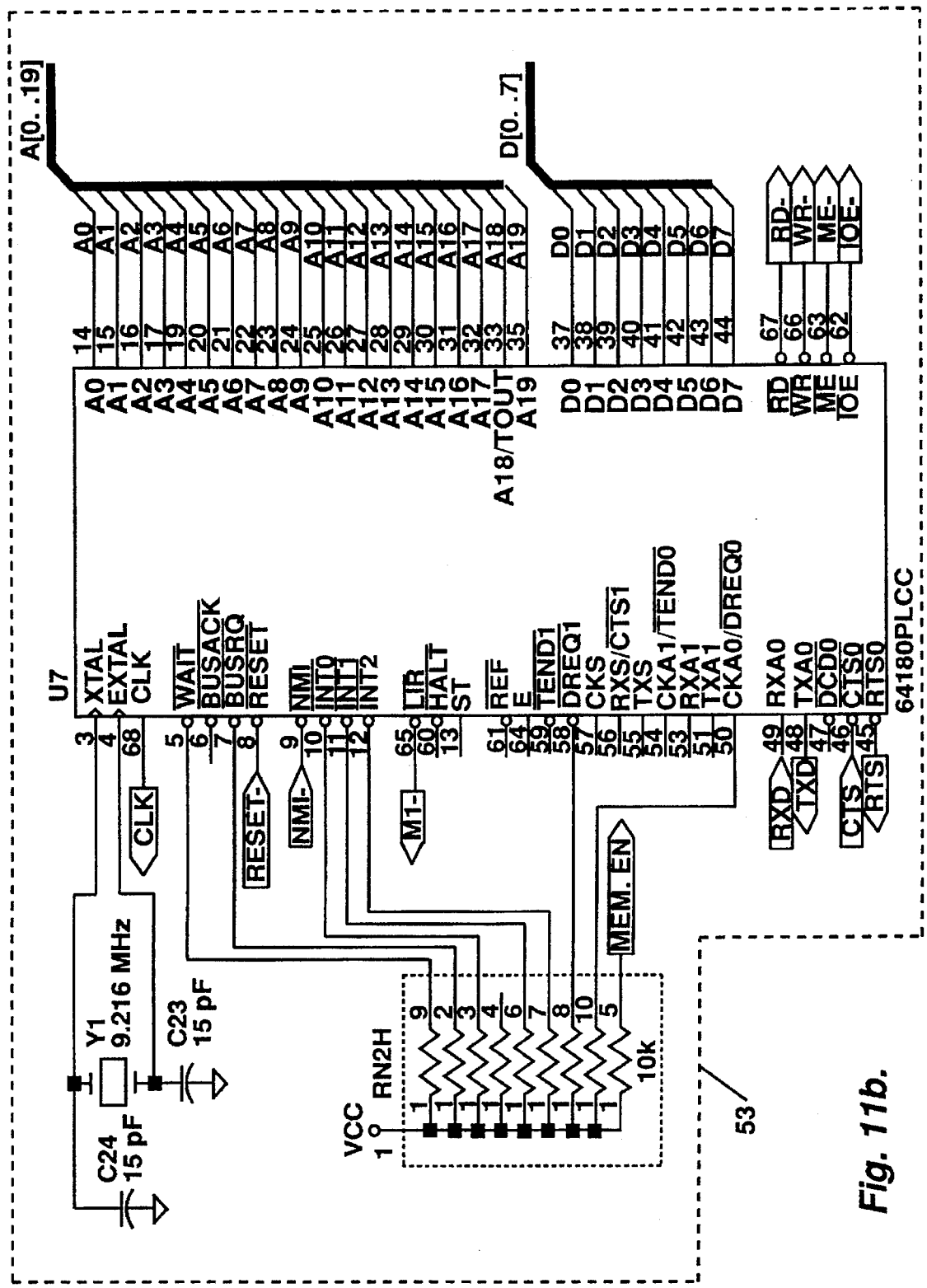
Figure 11C:
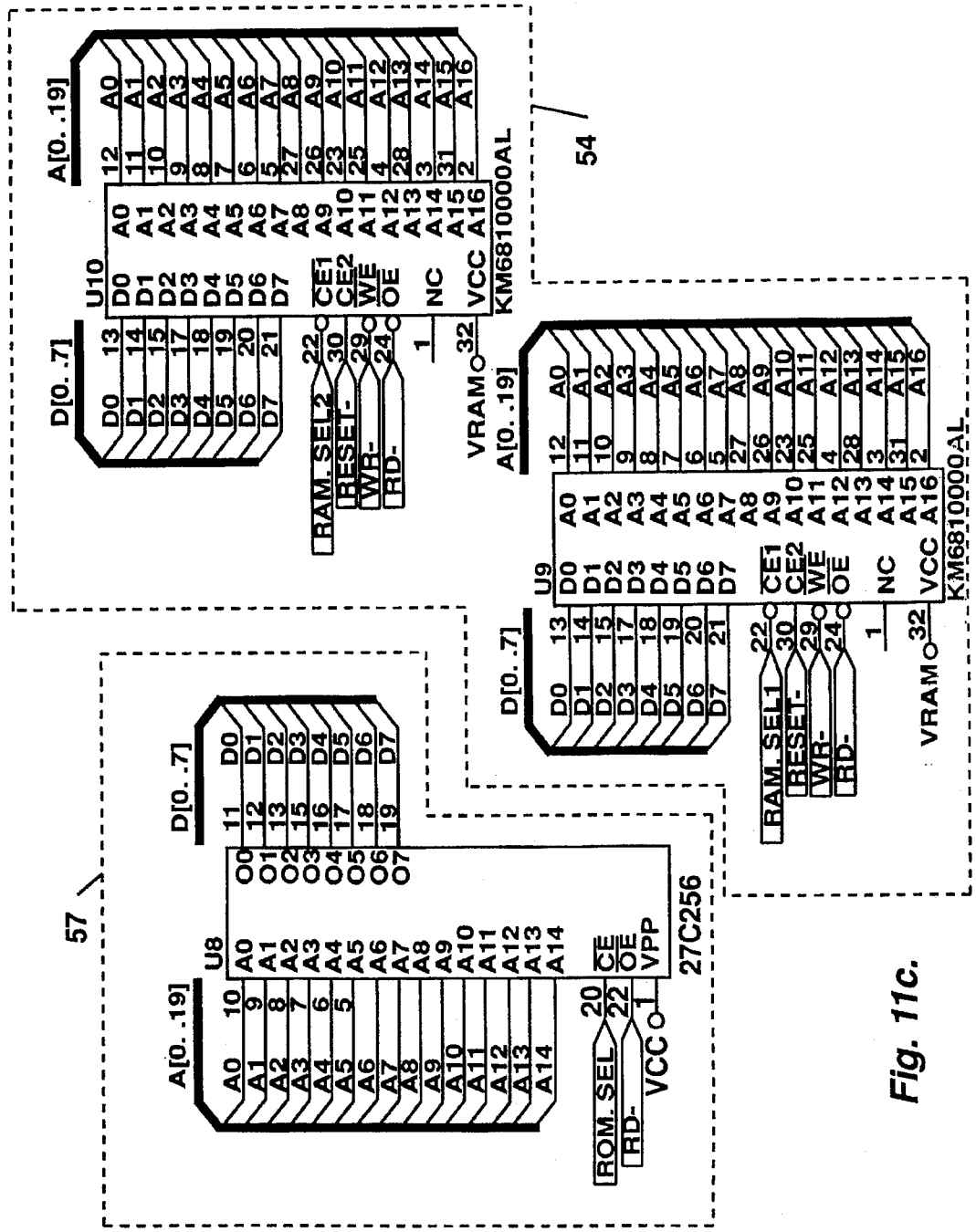
Figure 11D:
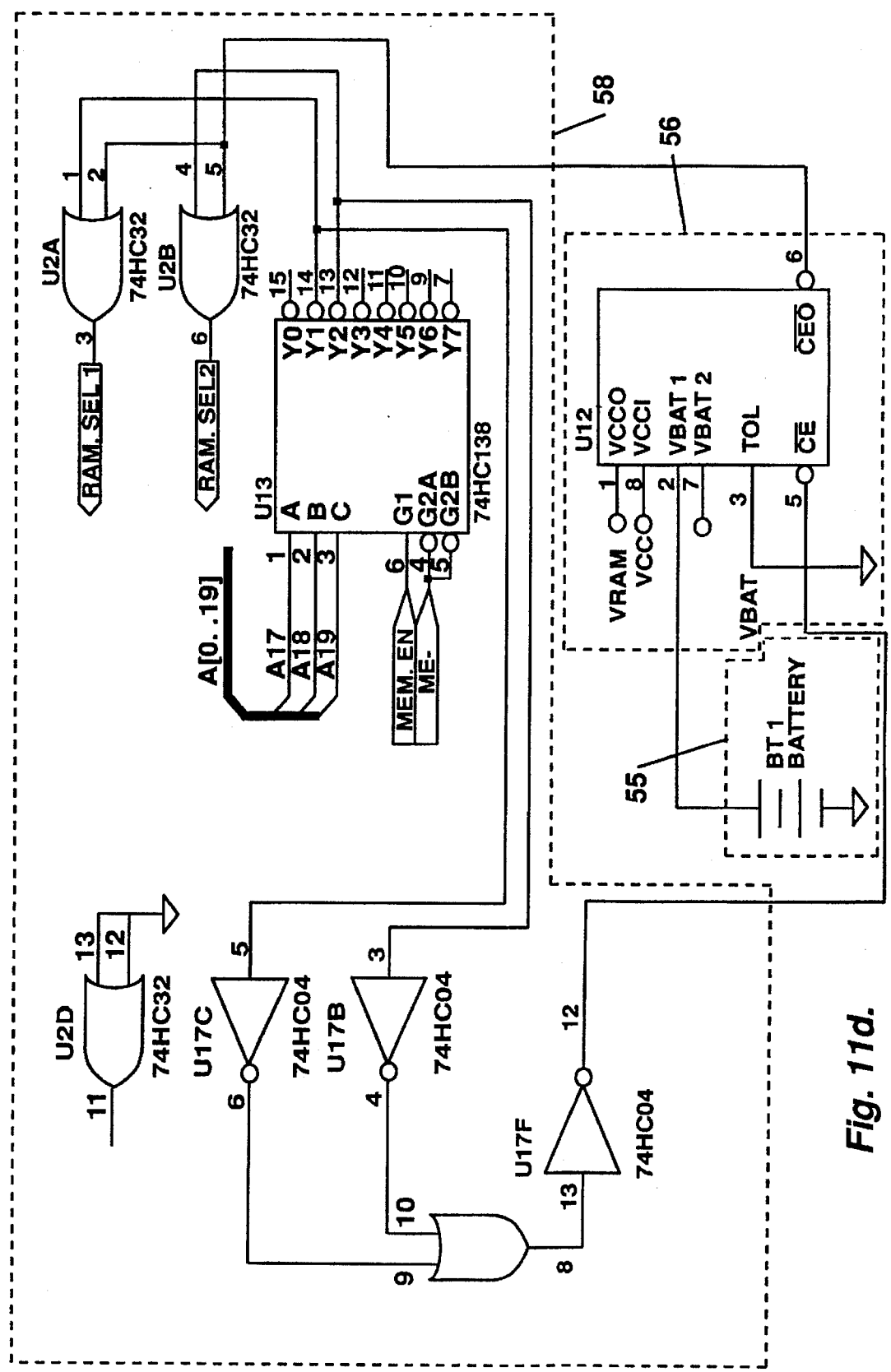
Figure 11E:
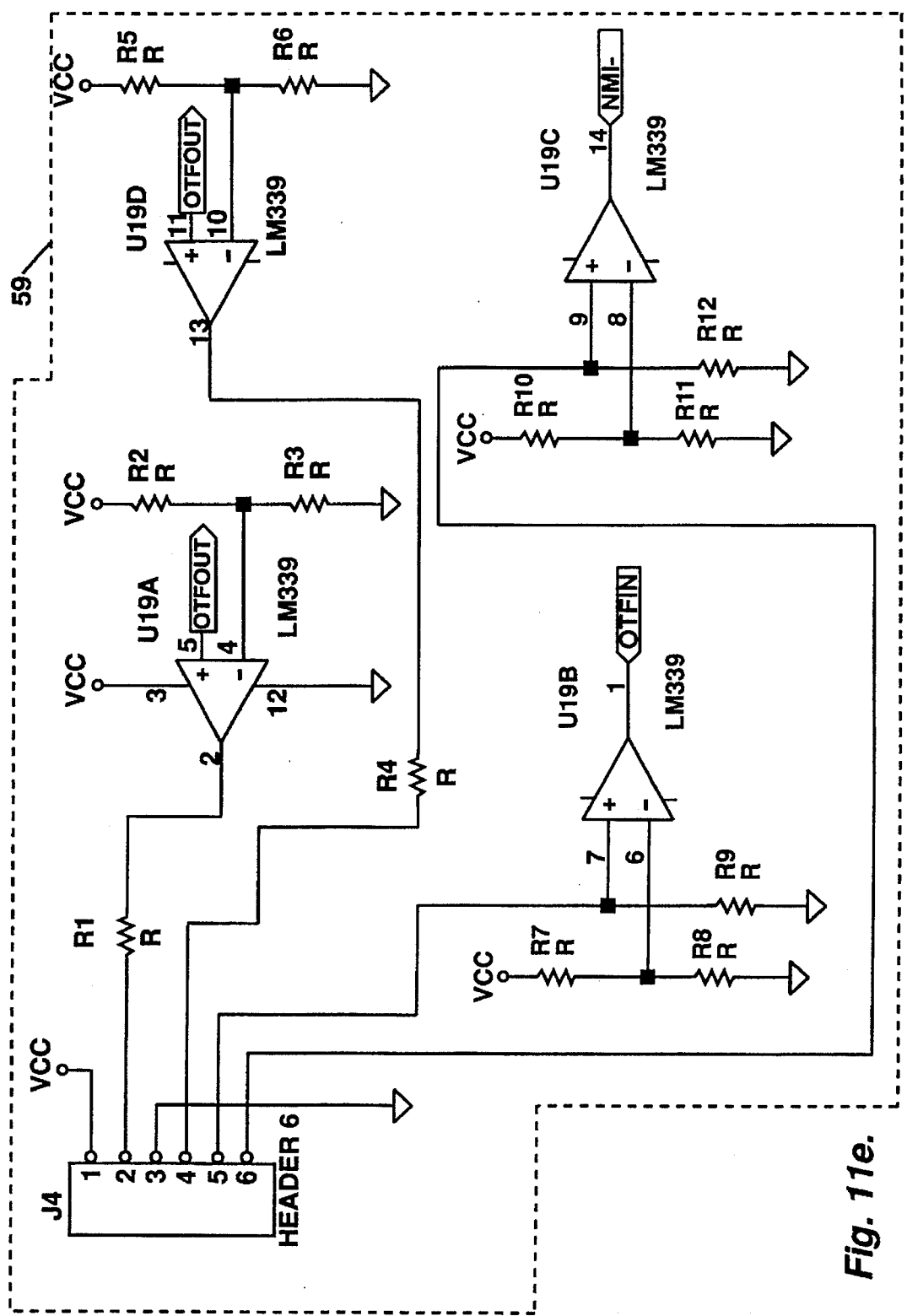
Figure 11F:
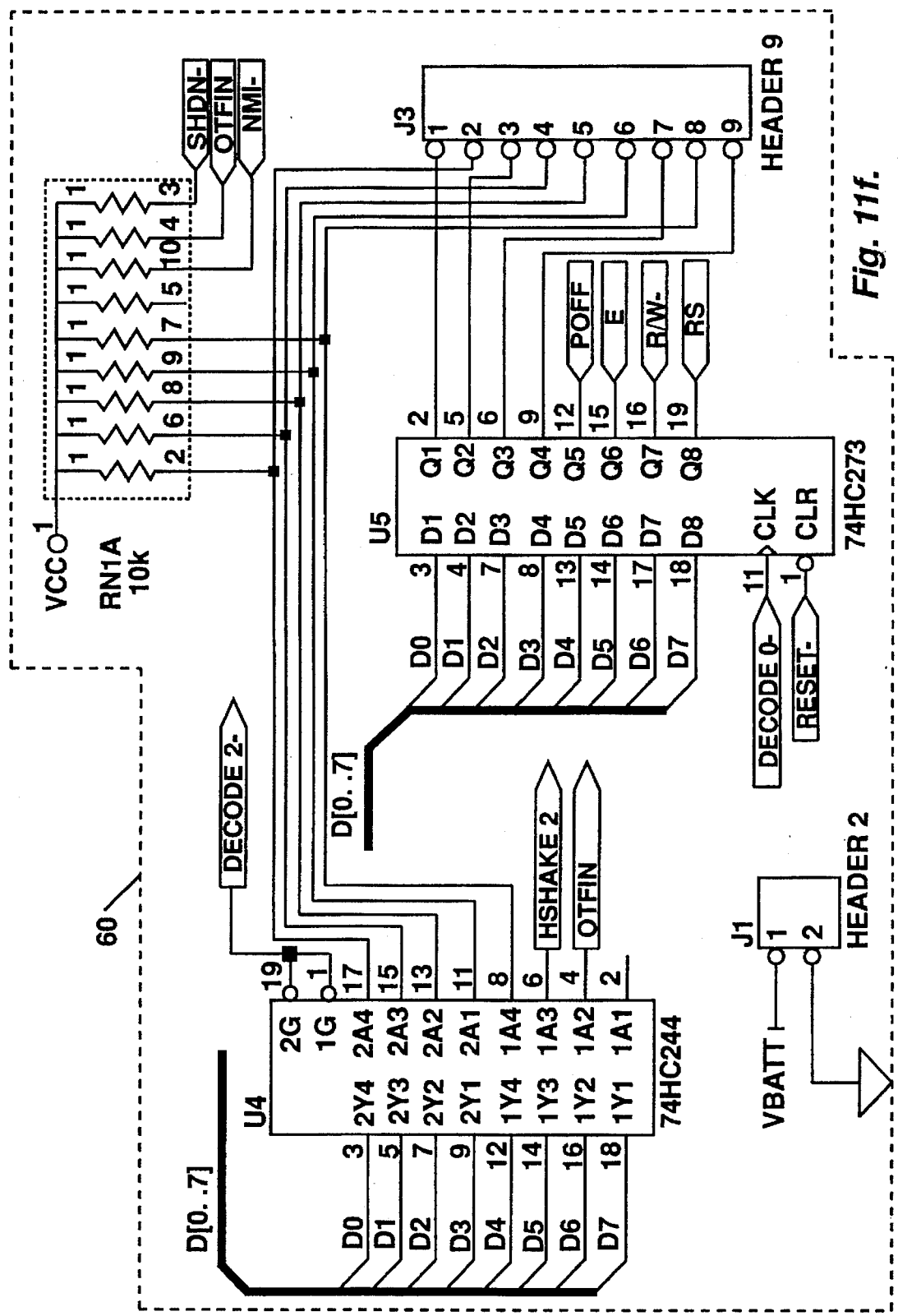
Figure 11G:
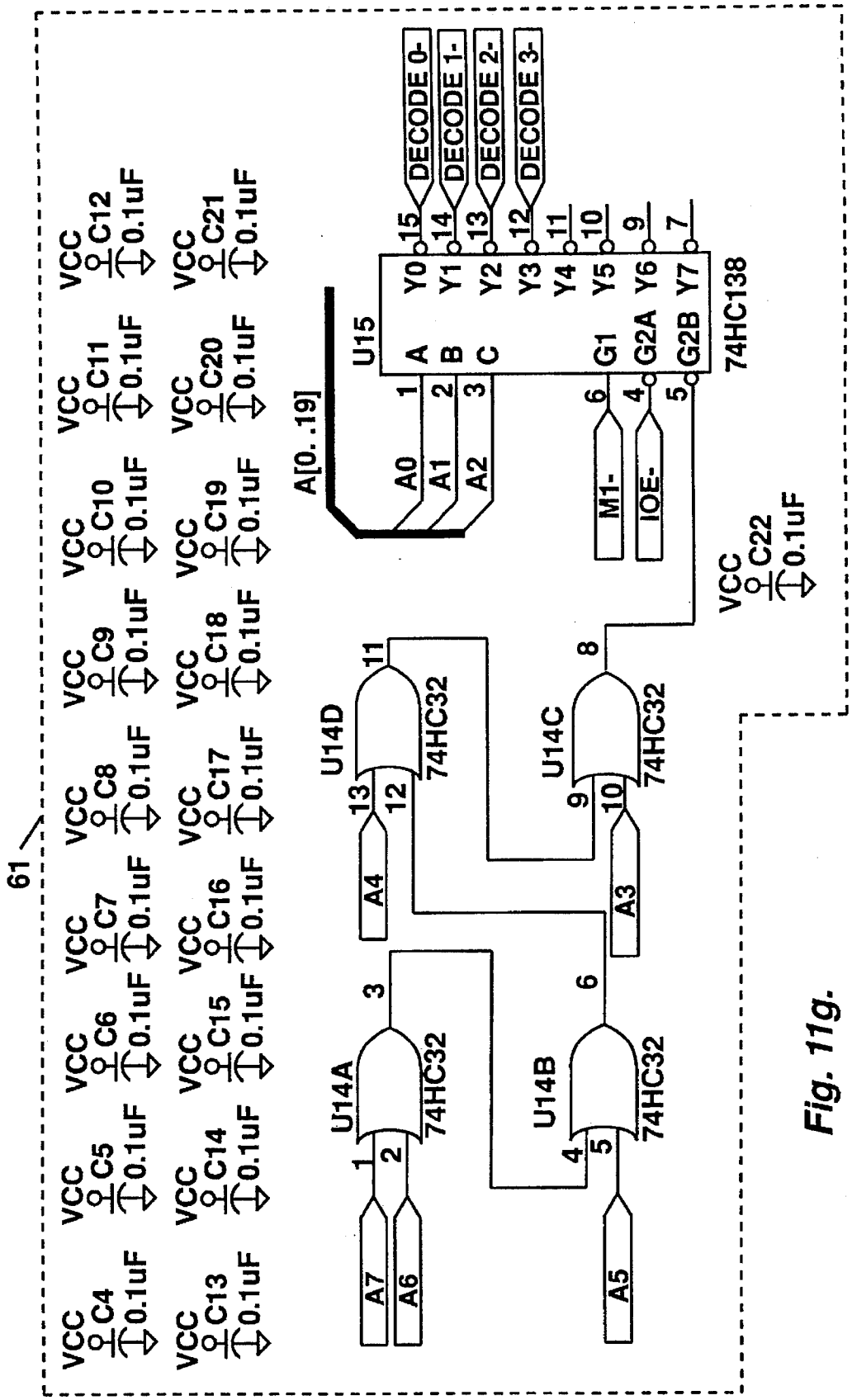
Figure 11H:
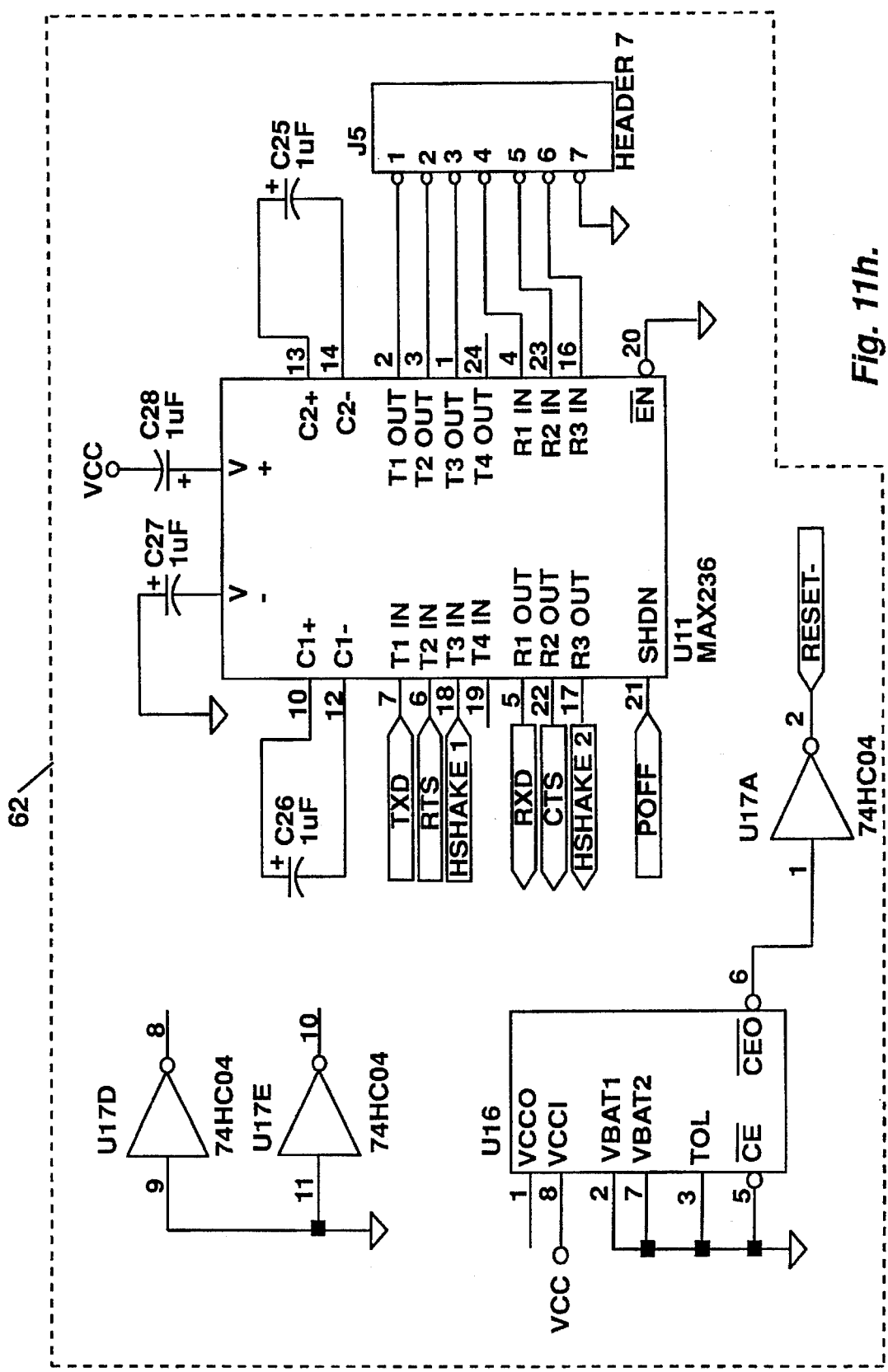
Figure 11I:
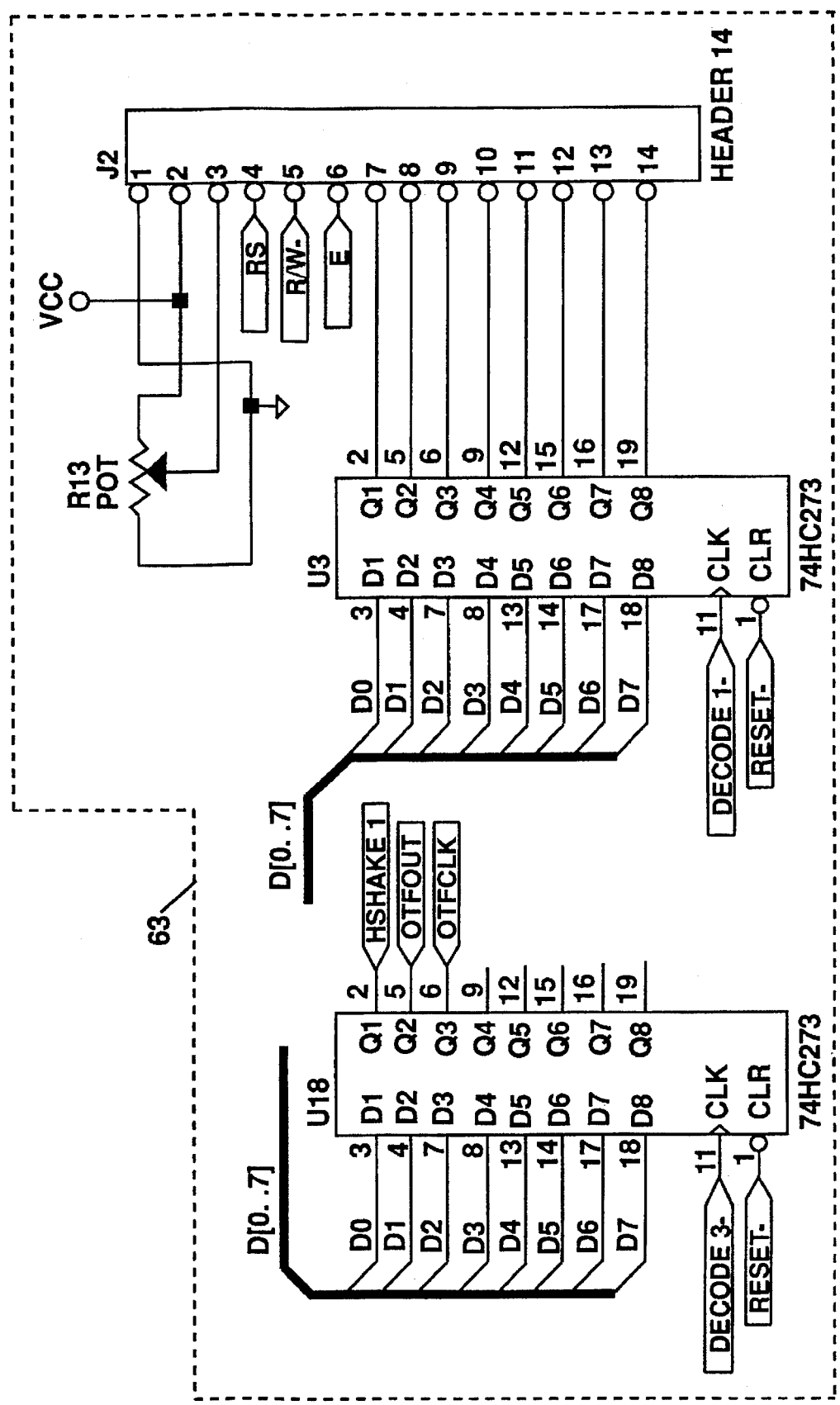

A schematic for the memory readout unit 40 is shown in FIG. 9; and a wiring diagram for this unit, by major components thereof, in FIGS. 11A–11I. The respective electrical components corresponding to the blocks on the schematic (FIG. 9) are as follows:

| Component | Reference Numeral | Wiring Diagram (FIG. No.) |
|---|---|---|
| Power Supply | 52 | 11A |
| Microprocessor | 53 | 11B |
| Ram Image Memory | 54 | 11C |
| Backup Battery | 55 | 11D |
| Supervisory Circuits | 56 | 11D |
| EPROM Program | 57 | 11C |
| RAM Select | 58 | 11D |
| Optical Data Link | 59 | 11E |
| Keyboard | 49 | 7, 8 |
| Keyboard Interface | 60 | 11F |
| Decode Logic | 61 | 11G |
| Serial Interface | 62 | 11H |
| ICD Display | 50 | 7, 8 |
| Display Driver | 63 | 11I |

It is understood that those skilled in the art may conceive other applications, modifications and/or changes in the invention described above. Any such applications, modifications or changes which fall within the purview of the description are intended to be illustrative and not intended to be limitative. The scope of the invention is limited only by the scope of the claims appended hereto.

It is claimed:

1. A system comprising:
   (a) means, including at least one spring biased in compression, for applying extraoral force;
   (b) means for measuring magnitude of the extraoral force and for measuring time during which the extraoral force is applied, the measuring means including an elongated magnet which moves longitudinally as compression forces acting on the spring change its extension and a magnetic flux detector for detecting a changing magnetic field as the elongated magnet moves longitudinally and for producing a voltage proportional in magnitude to changes in the magnetic field; and
   (c) means for recording information as to the magnitude of the extraoral force and the time the force is applied.

2. The system according to claim 1 which further comprises means for extracting and reading the information as to the magnitude of the extraoral force and the time the force is applied.

3. A device for use in placing a tension force on an outer bow of an orthodontic apparatus, adapted for use on a patient, and in storing a history of that force, comprising:
   (a) a case;
   (b) at least one elongated spring biased in compression;
   (c) a stop against which one end of the elongated spring abuts, the stop being housed in the case;
   (d) belt means for maintaining the stop in a relatively fixed position relative to the patient's jaw;
   (e) means, including a strap, for compressing the spring by pulling an end thereof disposed distal from the stop towards the patient's mouth;
   (f) means for adjusting magnitude of the tension force, the adjusting means including a screw which is threadedly engaged with the case for repositioning the stop;
   (g) means for measuring the tension force applied to the outer bow, the tension force measuring means including an elongated magnet, a magnetic flux sensor, and an electronic circuit, the magnet being disposed parallel to the spring and travelling a distance proportional to any change in length of the spring, the magnetic flux sensor detecting changing magnetic fields of the magnet as the magnet travels and producing a corresponding electronic signal, and the electronic circuit converting this signal into force units; and
   (h) means, including a digital circuit and time and memory electronic modules, for storing each measurement of the tension force and time when the measurement was made.

4. The device according to claim 3 which further comprises means for processing each measurement of the tension force and time when the measurement was made into a convenient format.

\* \* \* \* \*